United States Patent [19]

Fahmy et al.

[11] 4,298,617

[45] Nov. 3, 1981

[54] SYMMETRICAL AND ASYMMETRICAL SULFINYL-DICARBAMATES

[75] Inventors: Mohamed A. H. Fahmy; Tetsuo R. Fukuto, both of Riverside, Calif.

[73] Assignee: Regents of University of California, Los Angeles, Calif.

[21] Appl. No.: 18,414

[22] Filed: Mar. 7, 1979

[51] Int. Cl.³ .................. A01N 37/28; C07C 83/10
[52] U.S. Cl. .................. 424/298; 260/453 RW; 260/340.9 R; 424/300; 564/101
[58] Field of Search .............. 260/453 RW; 424/298

[56] References Cited

U.S. PATENT DOCUMENTS 4,004,031  1/1977  Drabek .................. 424/298

Primary Examiner—Henry R. Jiles
Assistant Examiner—Robert C. Whittenbaugh
Attorney, Agent, or Firm—Herzig & Walsh, Inc.

[57] ABSTRACT

A novel class of chemical compounds useful as pesticides consists of symmetrical and asymmetrical N,N'-sulfinyldicarbamate esters. The preparation of these compounds and their formulation to control insects are exemplified.

31 Claims, No Drawings

SYMMETRICAL AND ASYMMETRICAL SULFINYL-DICARBAMATES

BACKGROUND OF THE INVENTION

This invention relates to the general field of pesticides, and is particularly concerned with the production of insecticides for the control of both household insects and crop insects.

U.S. Pat. No. 3,997,549 to Fukuto and Black discloses N-arylsulfenylated derivatives of benzofuranyl methylcarbamates as effective pesticides.

U.S. Pat. No. 4,006,231 to Black and Fukuto discloses N-aminosulfenylated derivatives of carbofuran as effective pesticides.

U.S. Pat. No. 3,843,689 to Brown discloses production of N-methyl- or N-phenyldithiocarbamates produced from N-chlorothiocarbamates, as insecticides.

The article "Selective Toxicity of N,N'-Thiodicarbamates" by M. A. H. Fahmy, N. M. Mallipudi and T. R. Fukuto in "Agricultural and Food Chemistry," Vol. 26, No. 3, page 550, May/June, 1978, discloses a series of N-(alkyl alkylcarbamoylsulfenyl) derivatives of methylcarbamate as insecticides.

Application Ser. No. 636,623 of Liang, filed Dec. 1, 1975, and assigned to Union Carbide Corp., discloses asymmetrical bis-carbamoyl sulfide compounds containing the —N—S—N— group as active ingredients of pesticidal compositions.

The object of the present invention is to provide another novel class of carbamates which are effective pesticides, and procedure for preparing same.

SUMMARY OF THE INVENTION

The novel carbamate ester compounds of the invention are symmetrical and asymmetrical N,N'-sulfinyldicarbamate esters. The compounds can be prepared by reacting an N-chlorosulfinylcarbamate ester with aliphatic, aromatic and oxime carbamates, in a suitable organic solvent in the presence of a hydrogen chloride acceptor such as pyridine.

The resulting compounds of the invention are highly effective against certain pests and insects, and have substantially reduced mammalian toxicity, e.g. as compared to other potent insecticides such as carbofuran described in U.S. Pat. No. 3,474,171. Thus, the invention compounds, while having high toxicity toward certain pests or insects, are relatively safe to mammals.

DETAILED DESCRIPTION OF THE INVENTION AND PREFERRED EMBODIMENTS

The sulfinyldicarbamate esters or compounds of the invention have the formula noted below:

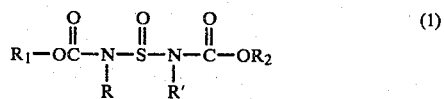

wherein R and R' are each a hydrocarbyl group containing from 1 to 12 carbon atoms, and R and R' can be the same or different; $R_1$ is selected from the class consisting of a hydrocarbyl group containing from 1 to 20 carbon atoms, a 5 to 6 membered heterocyclic ring containing O or S atoms, and a group containing the $>C=N-$ radical; and $R_2$ can be other than $R_1$ and selected from the class consisting of a hydrocarbyl group containing from 1 to 20 carbon atoms and a 5 to 6 membered heterocyclic ring containing O or S atoms; or $R_2$ can be the same as $R_1$.

Thus, R and R' are each a hydrocarbyl (hydrocarbon) group containing only hydrogen and carbon, either aliphatic or aromatic preferably a straight chain, branched or carbocyclic (five or six membered ring) alkyl, phenylalkyl or phenyl, and containing from 1 to 12 carbon atoms, and further exemplified hereinafter. R and R' can be the same or different.

$R_1$ can be a hydrocarbyl group containing from 1 to 20 carbon atoms, either aliphatic or aromatic, as further exemplified below; a 5 or 6 membered heterocyclic ring containing O or S atoms, e.g. benzothienyl, furanyl, benzofuranyl and 1,3-benzodioxolyl; or the $>C=N-$ group. The latter group can be represented more specifically by the formula:

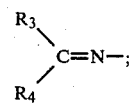

where
$R_3$ is hydrogen, alkyl, alkylthio or cyano, and
$R_4$ is alkyl, alkylthio, alkoxy, alkanoyl, alkoxycarbonyl, dialkylaminocarbonyl and phenyl, all of which can be unsubstituted or substituted with one or more cyano, nitro, alkylthio, alkylsulfinyl, alkylsulfonyl and alkoxy groups.

Where $R_1$ is aryl, preferred examples of such aryl groups are as follows:

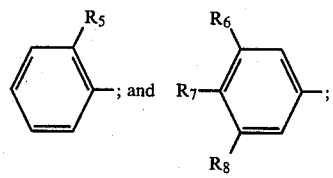

where
$R_5$ is hydrogen, alkoxy, alkylthio, alkyl, alkylthioalkyl, 2-dioxalanyl or halogen, e.g. Cl or Br;
$R_6$ is alkyl;
$R_7$ is hydrogen, alkyl, halogen, alkylthio, alkoxy, dialkylamino or formyl(alkyl)amino;
$R_8$ is hydrogen or alkyl;
and wherein the number of aliphatic carbon atoms in $R_3$, $R_4$, $R_5$, $R_6$, $R_7$, and $R_8$, individually, should not exceed eight; and $R_2$ can be other than $R_1$ and can be a hydrocarbyl group containing from 1 to 20 carbon atoms, either aliphatic or aromatic, e.g. substituted or unsubstituted alkyl, cycloalkyl, phenylalkyl, naphthylalkyl or aryl, such as phenyl or naphthyl, unsubstituted or substituted; or a five to six membered unsubstituted or substituted heterocyclic ring, which includes, in any combination, O or S atoms, e.g. one or two oxygen or sulfur atoms, e.g. furanyl; and wherein the substituents which can be present on the above groups can be one or more halogen, e.g. Cl or Br, cyano, nitro, dialkylamino, alkyl, alkylthio or alkoxy groups. $R_2$ also can be the same as $R_1$.

When R and R' are the same, and $R_1$ and $R_2$ are the same, the resulting compounds are symmetrical N,N'-sulfinyldicarbamates according to the invention. In the symmetrical carbamates where R and R' are phenyl or substituted phenyl, $R_1$ and $R_2$ can be alkyl groups containing from 1 to 10 carbon atoms such as isopropyl, and the like. When R and R' are different and/or $R_1$ and $R_2$ are different, the resulting compounds are asymmetrical N,N'-sulfinyldicarbamates, according to the invention.

Preferred carbamates of the invention are those of formula (1) above, where R is an alkyl group having from 1 to 4 carbon atoms, e.g. methyl, ethyl, propyl, isopropyl, butyl and isobutyl, preferably methyl, and R' is an alkyl group having from 1 to 8 carbon atoms, or phenyl. In such preferred carbamates $R_1$ and $R_2$ can be a hydrocarbyl group containing from 1 to 12 carbon atoms; heterocyclic rings containing O or S atoms, and containing 5 to 6 members in the heterocyclic nucleus; and groups containing the >C=N— radical. R and R' can be the same or different, and $R_1$ and $R_2$ can be the same or different.

Thus, in one group of preferred carbamate ester compounds of the invention, $R_1$ and $R_2$ are hydrocarbyl groups containing from 1 to 12 carbon atoms, either aliphatic or aromatic. These can include alkyl, e.g. methyl, ethyl, isopropyl, propyl, isobutyl, cycloalkyl, e.g. cyclohexyl, phenylalkyl, naphthylalkyl; aryl, e.g. phenyl, naphthyl such as 1-naphthyl, alkylphenyl, e.g. tolyl, xylyl or alkylnaphthyl, any of which can contain substituents such as dialkylamino, halogen, e.g. chlorine or bromine, alkoxy and alkylthio. Particularly preferred are those compounds where $R_1$ is alkylphenyl and alkoxyphenyl, and which can be unsubstituted or substituted, e.g. with halogen, alkoxy, dialkylamino, and the like, and especially wherein $R_1$ is 3-isopropylphenyl, 3-sec.-butylphenyl or 2-isopropoxyphenyl. Particularly preferred also is the group of carbamate esters wherein $R_1$ is a heterocyclic ring, and including fused-on heterocyclic rings containing O or S atoms, and 5 to 6 members in the heterocyclic nucleus, e.g. benzofuranyl or 1,3-benzodioxolyl, and especially a 2,3-dihydrobenzofuranyl-7 group having the formula (2) below, and the 1,3-benzodioxol-4 group having the formula (2a) below.

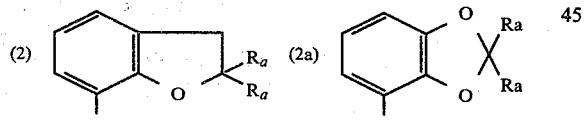

where $R_a$ is an alkyl group of 1 to about 4 carbon atoms, e.g. methyl, ethyl, propyl, n-butyl, and both $R_a$'s can be the same or different, and most preferably, wherein $R_1$ is the 2,3-dihydro-2,2-dimethylbenzofuranyl-7 group or the 2,2-dimethyl-1,3-benzodioxol-4 group. Another particularly preferred class of carbamates of the invention are those wherein $R_1$ is a group containing the >C=N— radical, as defined above. Such groups can be, for example, the following:

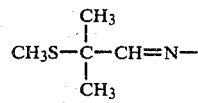

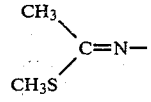

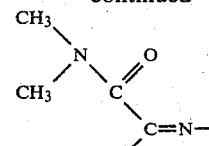

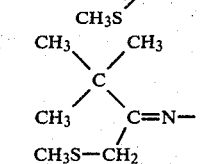

Particularly, but not necessarily, where the above preferred classes of compounds are asymmetrical, $R_2$ usually is alkyl, alkoxyalkyl, phenyl, alkylphenyl or alkoxyphenyl, preferably alkyl or alkoxyalkyl, of from 1 to 12 carbon atoms.

R and R' in all of the above preferred compounds is preferably alkyl, containing from 1 to 4 carbon atoms, e.g. methyl.

Where the above preferred classes of compounds are symmetrical, $R_2$ is the same as $R_1$, and R and R' are alkyl of from 1 to 4 carbon atoms, R and R' being the same. In the most preferred symmetrical N,N'-sulfinyldicarbamates, $R_1$ and $R_2$ are both benzofuranyl groups as defined above, or are both groups containing the >C=N— radical as defined above, or are both phenyl, alkylphenyl or alkoxyphenyl; and in all such compounds R and R' are both like alkyl groups of 1 to 4 carbon atoms, preferably methyl.

The symmetrical N,N'-sulfinyldicarbamates of the invention can be readily prepared in a one step process according to the following general reaction scheme:

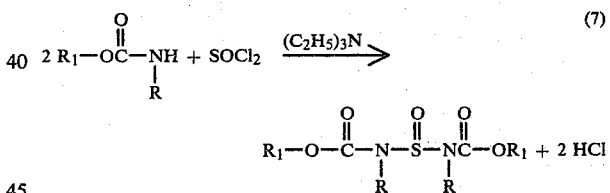

The above reaction of the carbamate ester starting material and thionyl chloride is carried out using a hydrogen chloride acceptor such as triethylamine in an inactive polar solvent such as tetrahydrofuran. The carbamate ester product can be formed in high yield employing two moles of the carbamate ester starting material per mole of thionyl chloride, at from 0° C. to 50° C., e.g. at room temperature (20° C.), using about two moles or a slightly greater proportion of hydrogen chloride acceptor, e.g. triethylamine, with respect to the carbamate starting material.

Symmetrical N,N'-sulfinyldicarbamates can also be prepared by the following reaction scheme:

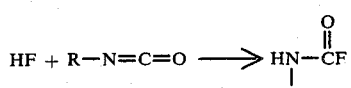

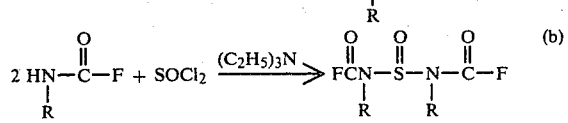

-continued

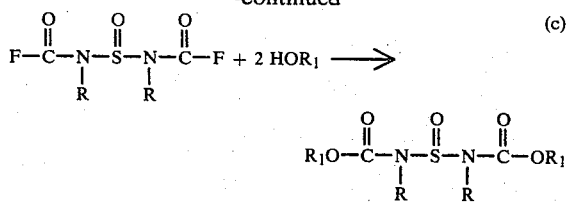

This procedure is less convenient as compared to the direct reaction of thionyl chloride with the carbamate. However, it can be useful if $R_1$ is substituted by functional groups that are susceptible to thionyl chloride such as unsubstituted or monoalkyl substituted amides or aromatic and aliphatic amines.

Asymmetrical N,N'-sulfinyldicarbamates can be prepared by reacting N-chlorosulfinylcarbamates with alkyl, aryl, or oxime carbamates as illustrated by the following equation:

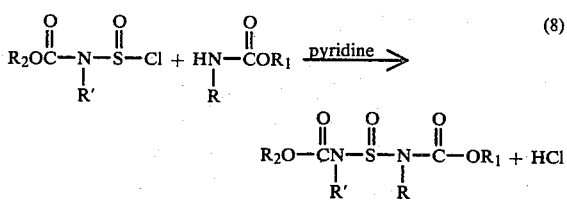

The N-chlorosulfinylcarbamate ester intermediate is formed by the reaction of the corresponding carbamate with thionyl chloride, preferably using pyridine as hydrogen chloride acceptor in an inactive polar solvent such as tetrahydrofuran. Non-polar solvents such as hexane also may be used. Such ester can be formed in high yield using essentially equivalent quantities of the carbamate and thionyl chloride and slightly more than an equivalent amount of pyridine. These novel intermediates are described in the copending application Ser. No. 18,416, filed Mar. 7, 1979, by M. A. H. Fahmy and T. R. Fukuto.

Without isolation, the N-chlorosulfinylcarbamate ester intermediate can react in situ with the carbamate in the presence of pyridine in slight excess to equivalent amounts, as a hydrogen chloride acceptor. Generally the reaction can be carried out from 0° C. to 50° C., e.g. at room temperature, but heating up to about 50° C. can be employed for relatively less reactive carbamates.

It will be understood that if desired, the N-chlorosulfinylcarbamate ester starting material in reaction (8) above can be initially prepared and isolated as an intermediate compound, and such compound then reacted with the appropriate carbamate ester in the presence of an HCl acceptor, as noted in the above equation (8), in an organic solvent such as dry methylene chloride or tetrahydrofuran, the amount of solvent used being the minimum, e.g. about 15-25 ml per 0.02 mol reactants, at temperatures noted above.

The reaction illustrated in equation (8) above can be carried out in an opposite manner, that is by reacting the N-chlorosulfinyl intermediate of aryl or oxime carbamates with aliphatic carbamates under the same reaction conditions. In all of the above reactions, R, R', $R_1$ and $R_2$ have the values defined above.

The following are examples of preparation of the carbamate ester compounds of the invention.

SYMMETRICAL N,N'-SULFINYLDICARBAMATES

EXAMPLE I

Synthesis of N,N'-sulfinyldi-(2,3-dimethyl-2,3-dihydrobenzofuranyl-7 methylcarbamate)

To a solution of 2,2-dimethyl-2,3-dihydrobenzofuranyl-7 methylcarbamate (4.4 g, 0.02 mol) in 20 ml dry tetrahydrofuran was added 1.2 g thionyl chloride (0.01 mol). The mixture was stirred and cooled in an ice-water bath (temperature <10° C.). Triethylamine (2.0 g, 0.02 mol) was added dropwise to the mixture. The temperature was allowed to rise up to room temperature after the complete addition of the amine. Stirring was continued for an additional one hour at room temperature, and 150 ml ether was added. The mixture was washed with water four times (25 ml each) and dried over anhydrous sodium sulfate. Evaporation of the solvent resulted in a solid material which was crystallized from benzene-hexane to give 3.5 g (yield 71.7%) of product, mp 139°-142° C.

Analysis calculated for $C_{24}H_{28}N_2O_7S$; carbon, 59.00%, hydrogen, 5.78%, Found: carbon, 59.60%; hydrogen, 5.54%.

EXAMPLE II

Synthesis of N,N'-sulfinyldi-(2-isopropoxyphenyl methylcarbamate)

To a solution of 2-isopropoxyphenyl methylcarbamate (4.2 g, 0.02 mol) in 20 ml dry tetrahydrofuran was added 1.2 g thionyl chloride and the mixture was cooled in an ice-water bath. Triethylamine (2.0 g, 0.02 mol) was added dropwise with stirring (temperature<10° C). Stirring was continued for 1 hour while temperature was allowed to rise up to room temperature. Workup and purification was similar to Example I yielding 2.7 g of product, m.p. 71°-74° C. after recrystallization from ether-hexane.

Analysis calculated for $C_{22}H_{28}N_2O_7S$; carbon, 56.88%; hydrogen, 6.08%. Found: carbon, 57.31%; hydrogen, 6.00%.

EXAMPLE III

Synthesis of N,N'-sulfinyldi-[S-methyl N''-(methylcarbamoyloxy)thioacetimidate

To a solution of S-methyl N-(methylcarbamoyloxy)-thioacetimidate (3.3 g, 0.02 mol) in 20 ml dry tetrahydrofuran was added 1.2 g thionyl chloride (0.01 mol). The mixture was cooled in an ice-water bath. Triethylamine (2.0 g, 0.02 mol) was added dropwise with stirring, and the temperature was allowed to rise up to room temperature after the complete addition of the amine. Stirring was continued at room temperature for one hour and the reaction mixture was worked up using chloroform in place of ether as used in the other examples. The product was crystallized from chloroform-ether mixture yielding 2.2 g of material m.p. 142°-143° C.

Analysis calculated for $C_{10}H_{18}N_4O_5S_3$; carbon, 32.45%; hydrogen, 4.90%. Found: carbon, 32.86%; hydrogen, 5.02%.

EXAMPLE IV

Synthesis of N,N'-sulfinyldi[2-methyl-2-(methylthio)propionaldehyde O-(methylcarbamoyl)-oxime]

To a solution of 2-methyl-2-(methylthio)propionaldehyde O-(methylcarbamoyl)-oxime (4.0 g, 0.02 mol) in 20 ml dry tetrahydrofuran was added 1.2 g thionyl chloride (0.01 mol) and the mixture was cooled in an ice-water bath. While stirring, 2.0 g triethylamine (0.02 mol) was added dropwise and stirring was continued for an additional one hour. The mixture was diluted with 150 ml ether and worked up similarly to the other examples. The crude product was crystallized from ether-hexane to give 3.1 g of the product noted above, m.p. 61°–63° C.

Analysis calculated for $C_{14}H_{26}N_4O_5S_3$; carbon, 39.42%; hydrogen, 6.14%. Found: carbon, 39.84%; hydrogen, 5.96%.

ASYMMETRICAL N,N'-SULFINYLDICARBAMATES

EXAMPLE V

Synthesis of S-methyl N-[N'-(N''-ethyl-N''-(n-propoxycarbonylaminosulfinyl)-N'-methylcarbamoyloxy]thioacetimidate.

To a solution of S-methyl N-(N'-methylcarbamoyloxy)thioacetimidate (3.3 g, 0.02 mol) in 20 ml anhydrous dichloromethane, was added 4.3 g of propyl (ethyl)(chlorosulfinyl)carbamate (prepared from propyl ethylcarbamate and thionyl chloride, b.p. 65°–69° C. at 0.5 mm) and 1.6 g (0.02 mol) anhydrous pyridine. The mixture was stirred for twelve hours at room temperature. Ether (100 ml) was added and the mixture was washed with water three (30 ml each) times. The ether solution was dried over anhydrous sodium sulfate, filtered and concentrated under vacuum. A sample of the oily residue was purified by preparative thin-layer chromatography using ether-hexane (3:1) mixture as the developing solvent.

Analysis calculated for $C_{11}H_{21}N_3O_5S_2$; carbon, 38.92%; hydrogen, 6.23%. Found: carbon, 38.38%; hydrogen, 5.78%.

EXAMPLE VI

Synthesis of S-methyl N-[N'-(N''-methyl-N''-(n-propoxycarbonylaminosulfinyl)-N'-methylcarbamoyloxy]thioacetimidate.

A mixture of S-methyl N-(N'-methylcarbamoyloxy)thioacetimidate (3.3 g, 0.02 mol), pyridine (2.0 g, 0.025 mol), propyl (methyl)(chlorosulfinyl)carbamate (4.3 g, 0.021 mol, prepared from propyl methylcarbamate and thionyl chloride, b.p. 78°–79° C. at 2.5 mm) in 20 ml anhydrous tetrahydrofuran was stirred overnight at room temperature. Ether (100 ml) was added and the mixture was worked up and purified similarly to Example V.

Analysis calculated for $C_{10}H_{19}N_3O_5S_2$; carbon, 36.91%; hydrogen, 5.89%. Found: carbon, 37.65%; hydrogen, 6.47%.

EXAMPLE VII

Synthesis of 2,3-dihydro-2,2-dimethylbenzofuranyl-7 N-[N'-(methoxycarbonyl)-N'-(methylaminosulfinyl)]-N-methylcarbamate.

To a solution of 2,3-dihydro-2,2-dimethylbenzofuranyl-7 methylcarbamate (5.5 g, 0.025 mol) and pyridine (2.8 g, 0.035 mol) in 15 ml dichloromethane was added methyl (methyl)(chlorosulfinyl)carbamate (6.0 g, 0.035 mol, b.p. 66°–68° C. at 3.0 mm). The mixture was stirred at room temperature for 12 hours. Ether, 150 ml, was added and the mixture was worked up similar to previous examples to give an oily residue which was subjected to high vacuum to remove unreacted methyl methylcarbamate. The residue weighed 8.4 g, 98% yield. An analytical sample was obtained using preparative thin-layer chromatography.

Analysis calculated for $C_{15}H_{20}N_2O_6S$; carbon, 50.55%; hydrogen, 5.66%. Found: carbon, 51.16%; hydrogen, 5.84%.

EXAMPLE VIII

Synthesis of 2,3-dihydro-2,2-dimethylbenzofuranyl-7 N-[N'-(ethoxycarbonyl)-N'-(methylaminosulfinyl)]-N-methylcarbamate.

A mixture of 2,3-dihydro-2,2-dimethylbenzofuranyl-7 methylcarbamate (5.5 g, 0.025 mol), pyridine (2.8 g, 0.035 mol) and ethyl (methyl)(chlorosulfinyl)carbamate (6.5 g, 0.035 mol, b.p. 58°–60° C. at 1.2 mm) in 20 ml dichloromethane was stirred at room temperature for 12 hours. The reaction mixture was worked up similarly to Example VII.

Analysis calculated for $C_{16}H_{22}N_2O_6S$; carbon, 51.88%, hydrogen, 5.98%. Found: carbon, 52.33%; hydrogen, 6.98%.

EXAMPLE IX

Synthesis of 2,3-dihydro-2,2-dimethylbenzofuranyl-7 N-[N'-(n-propoxycarbonyl)-N'-(methylaminosulfinyl)]-N-methylcarbamate.

A mixture of 2,3-dihydro-2,2-dimethylbenzofuranyl-7 methylcarbamate (5.5 g, 0.025 mol), pyridine (2.8 g, 0.035 mol and n-propyl (methyl)(chlorosulfinyl)carbamate (b.p. 78°–79° C. at 2.5 mm, 6.7 g, 0.034 mol) in 20 ml anhydrous dichloromethane was stirred at room temperature for 12 hours. The reaction mixture was worked up and purified similarly to Example VII.

Analysis calculated for $C_{17}H_{24}N_2O_6S$; carbon, 53.10%; hydrogen, 6.29%. Found: carbon, 53.15%; hydrogen, 6.29%.

EXAMPLE X

Synthesis of 2,3-dihydro-2,2-dimethylbenzofuranyl-7 N-[N'-(n-heptoxycarbonyl)-N'-(methylaminosulfinyl)]-N-methylcarbamate.

A mixture of 2,3-dihydro-2,2-dimethylbenzofuranyl-7 methylcarbamate (1.1 g, 0.005 mol), pyridine (0.5 g, 0.006 mol) and n-heptyl (methyl)(chlorosulfinyl)carbamate (b.p. 98–100/0.05 mm 1.3 g, 0.0054 mol) in 5 ml dichloromethane was allowed to stand at room temperature overnight and ether (25 ml) was added. Workup and purification were similar to the previous examples.

Analysis calculated for $C_{21}H_{32}N_2O_6S$; carbon, 57.25%; hydrogen, 7.32%. Found: carbon: 57.56%; hydrogen, 7.32%.

EXAMPLE XI

Synthesis of 2-isopropoxyphenyl N-[N'-(n-propoxycarbonyl)-N'-(methylaminosulfinyl)]-N-methylcarbamate.

A mixture of 2-isopropoxyphenyl methylcarbamate (4.0 g, 0.02 mol), pyridine (2 g, 0.025 mol), and n-propyl (methyl) (chlorosulfinyl)carbamate (4.5 g, 0.023 mol), in 15 ml dichloromethane, was stirred at room temperature for 12 hours. The reaction mixture was worked up similarly to the other examples, and a sample was purified by preparative thin-layer chromatography using ether-hexane (3:1) as the developing solvent.

Analysis calculated for $C_{16}H_{24}N_2O_6S$; carbon, 51.55%; hydrogen, 6.44%. Found: carbon, 51.11%; hydrogen, 6.98%.

EXAMPLE XII

Synthesis of 3-isopropylphenyl N-[N'-(methoxycarbonyl)-N'-(methylaminosulfinyl)]-N-methylcarbamate.

A mixture of 3-isopropylphenyl methylcarbamate (3.8 g, 0.02 mol), pyridine (2 g, 0.025 mol), and methyl (chlorosulfinyl)(methyl)carbamate (4.3 g, 0.025 mol) in 15 ml dichloromethane, was stirred at room temperature for 12 hours. The reaction mixture was worked up similarly to previous examples and a sample was purified by preparative thin-layer chromatography using ether-hexane (3:1) as the developing solvent.

Analysis calculated for $C_{14}H_{20}N_2O_5S$; carbon, 51.20%; hydrogen, 6.14%. Found: carbon, 52.06%; hydrogen, 6.14%.

The following are additional examples of the N,N'-sulfinyldicarbamates of the invention.

S-Methyl N-[N'-(N''-ethyl-N''-(ethoxycarbonyl)aminosulfinyl)-N'-methylcarbamoyloxy]thioacetimidate S-Methyl N-[N'-(N''-methyl-N''-(benzyloxycarbonyl)aminosulfinyl)-N'-methylcarbamoyloxy]thioacetimidate S-Methyl N-[N'-(N''-methyl-N''-(2-methoxyethoxycarbonylaminosulfinyl)-N'-methylcarbamoyloxy]thioacetimidate S-Methyl N-[N'-(N''-methyl-N''-(2-isopropoxyphenoxycarbonylaminosulfinyl)-N'-methylcarbamoyloxy]thioacetimidate 2-Methyl-2-(methylthio)propionaldehyde O-[N-methyl-N-(N'-butoxycarbonyl-N'-methylaminosulfinyl)carbamoyl]-oxime S-Methyl N',N'-dimethyl-N-(N''-isopropoxycarbonyl-N''-methylaminosulfinyl)(methyl)carbamoyloxy-1-thiooximidate 2,2-Dimethyl-1,3-benzodioxolyl-4 N-(N'-isopropoxycarbonyl-N'-methylaminosulfinyl)-N-methylcarbamate 2,3-Dihydro-2,2-dimethylbenzofuranyl-7 N-(N'-2-ethoxy-ethoxycarbonyl-N'-methylaminosulfinyl)-N-methylcarbamate 2,3-Dihydro-2,2-dimethylbenzofuranyl-7 N-(N'-2-nitroethoxy carbonyl-N'-methylaminosulfinyl)-N-methylcarbamate 2,3-Dihydro-2,2-dimethylbenzofuranyl-7 N-(N'-2-methylthioethoxycarbonyl-N'-methylaminosulfinyl)-N-methylcarbamate 2,3-Dihydro-2,2-dimethylbenzofuranyl-7 N-(N'-2,2,2-trichloroethoxycarbonyl-N'-methylaminosulfinyl)-N-methylcarbamate 2-Chlorophenyl N-(N'-butoxycarbonyl-N'-ethylaminosulfinyl)-N-methylcarbamate 3-Methyl-4-dimethylaminophenyl N-(N'-isopropoxycarbonyl-N'-methylaminosulfinyl)-N-methylcarbamate 3,5-Dimethyl-4-methylthiophenyl N-(N'-isopropoxycarbonyl-N'-methylaminosulfinyl)-N-methylcarbamate N,N'-sulfinyldi-[S-methyl N'',N''-dimethyl-N'''-methyl carbamoyloxy-1-thio-oximidate]

N,N'-sulfinyldi-[3,3-dimethyl-1-(methylthio)butanone O-methylcarbamoyloxime]

2,3-Dihydro-2,2-dimethylbenzofuranyl-7 N-[(N'-isopropoxycarbonyl)-N'-(methylaminosulfinyl)]-N-methylcarbamate Particularly preferred compounds are the last three compounds in the above list, and the compounds of Examples III and IV above.

The insecticidal symmetrical and asymmetrical sulfinyldicarbamate esters of the invention may be formulated with the usual carriers, including additives and extenders used in the preparation of insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material. The present compounds may be made into liquid concentrates by solution or emulsification in suitable liquids such as organic solvents, and into solid concentrates by admixing with talc, clays and other known solid carriers used in the insecticide art. These concentrates are compositions containing about 5–50% toxicant and the rest inert material which includes dispersing agents, emulsifying agents, and wetting agents. The concentrates are diluted for practical application, with water or other liquid for liquid sprays or with additional solid carrier for application as a dust or granular formulation.

The concentration of the toxicant in the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative compounds of the N,N'-sulfinyldicarbamate esters of the invention were tested for insecticidal activity against two insect species, house flies, Musca domestica, and mosquito larvae, Culex pipiens. Stock 1% concentrated solutions of each of the test compounds were made in acetone, and such solutions diluted with acetone to a concentration of 0.001–0.1%. House flies were treated topically on the notum by 1 μl of each of the diluted acetone solutions and percent mortality was counted 24 hours after application. Insects were held at a constant temperature of 60° F. Larvicidal activity was determined by applying 1 ml of the acetone solution in 100 ml of water containing 20

3rd instar mosquito larvae. Results are presented as $LD_{50}$ in μg/g for house flies and $LC_{50}$ in ppm for mosquito larvae.

Mammalian toxicity was determined against Swiss white mice. The test compound was applied orally using corn oil or propylene glycol as the carrier, depending upon solubility of the compound therein. Results are given as $LD_{50}$ in mg of compound per kg body weight. The toxicological data for a number of typical compounds of the invention are summarized in Table I.

The term "$LD_{50}$" represents the dose needed to kill 50% of the test animals, the term "$LC_{50}$" is the concentration needed to kill 50% of the mosquito larvae. In interpreting the values in the table below, the lower the value for $LD_{50}$ for house flies and for $LC_{50}$ for mosquito larvae, the greater the insecticidal potency or toxicity of that particular compound. On the other hand, the higher the value of $LD_{50}$ for mice, the lower the mammalian toxicity or the greater is the mammalian safety of such compound.

TABLE I
Toxicity of symmetrical and asymmetrical N,N'-sulfinyldicarbamates against house flies, mosquito larvae and white mice

| Compound of Example | House flies $LD_{50}(\mu g/g)$ | Culex $LC_{50}(ppm)$ | Mice $LD_{50}(mg/kg)$ |
|---|---|---|---|
| I - Symmetrical Sulfinyldicarbamates | | | |
| I | 20 | | 165 |
| II | 85 | | 940 |
| III | 40 | | 210 |
| IV | 6.5 | | 1.8 |
| II - Asymmetrical Sulfinyldicarbamates | | | |
| V | 7.0 | | 115 |
| VI | 6.6 | | 160 |
| VII | 9.0 | | 62 |
| VII | 13.0 | 0.04 | 56 |
| IX | 9.0 | | 100 |
| X | 13.5 | 0.015 | 150 |
| XI | 20 | 0.18 | 500-1000 |
| XII | 80 | | 70 |
| 3-isopropylphenyl N-[N'-(ethoxycarbonyl)-N'-(methylaminosulfinyl)]-N-methylcarbamate | 75 | | 50-100 |

The relatively low values of the various compounds of the invention listed in Table I for $LD_{50}$ for house flies and $LC_{50}$ for mosquito larvae (Culex) indicates high toxicity of the invention compounds as against such insects. Thus, for example the parent material of the compounds of Examples VII to X of Table I, carbofuran, which is 2,3-dihydro-2,2-dimethyl-7-benzofuranyl methylcarbamate, has an $LD_{50}$ value for house flies, of about 6.5.

The $LD_{50}$ values for house flies of the related invention compound of Examples VII to X are comparable, ranging from 9 to 13.5, thus showing comparable insecticidal toxicity of such invention compounds to the potent insecticide carbofuran. However, and of particular significance, the mammalian toxicity of the invention compounds of Examples VII to X of Table I above, as indicated by their high $LD_{50}$ values ranging from 56 to 150 for mice, is low, as compared to the much higher toxicity as indicated by an $LD_{50}$ value of from about 2 to about 8, found for the parent carbamate ester insecticide, carbofuran. It is also noted that the $LD_{50}$ value of 940 and of 500-1000 for the compounds of Examples II and XI, respectively, are much higher than the $LD_{50}$ value of 60 found for the parent 2-isopropoxyphenyl methylcarbamate ester compound, which is the carbamate starting material in Examples II and XI; the $LD_{50}$ value of 50-100 for the compound of the last example of the table is substantially higher than the $LD_{50}$ value of 16 found for the parent 3-isopropylphenyl methylcarbamate ester compound, and the $LD_{50}$ value of 210 for the compound of Example III is much higher than the $LD_{50}$ value of 10 for the parent carbamate ester compound. Thus, the above Table shows that the N,N'-sulfinyldicarbamate esters of the invention have high insecticidal activity or potency, but have substantially reduced mammalian toxicity or substantially greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. Carbamates having pesticidal activity of the formula:

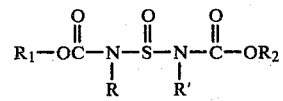

wherein R and R' are each a hydrocarbyl group containing 1 to 12 carbon atoms, and R and R' can be the same or different; $R_1$ is selected from the class consisting of a hydrocarbyl group containing from 1 to 20 carbon atoms, and a group containing the $>C=N-$ radical; and $R_2$ can be other than $R_1$ and selected from the class consisting of a hydrocarbyl group containing from 1 to 20 carbon atoms; or $R_2$ can be the same as $R_1$.

2. Symmetrical carbamates as defined in claim 1, wherein R and R' are the same, and $R_1$ and $R_2$ are the same.

3. Carbamates as defined in claim 1, wherein $R_1$ is the $>C=N-$ radical

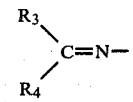

and where
  $R_3$ is hydrogen, alkyl, alkylthio or cyano, and
  $R_4$ is alkyl, alkylthio, alkoxy, alkanoyl, alkoxycarbonyl, dialkylaminocarbonyl, and phenyl, all of which can be unsubstituted or substituted with cyano, nitro, alkylthio, alkylsulfinyl, alkylsulfonyl and alkoxy groups, the number of aliphatic carbon atoms in $R_3$ and $R_4$ not exceeding eight.

4. Symmetrical carbamates as defined in claim 3, wherein both $R_1$ and $R_2$ are groups containing the $>C=N-$ radical, and R and R' are each an alkyl group, $R_1$ and $R_2$ being the same, and R and R' being the same.

5. Carbamates as defined in claim 1, wherein $R_1$ is an aryl group selected from the class consisting of:

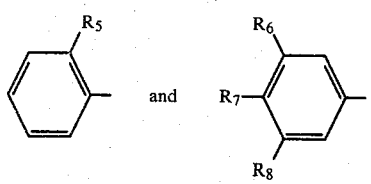

wherein
- R$_5$ is hydrogen, alkoxy, alkylthio, alkyl, alkylthioalkyl, 2-dioxalanyl or halogen;
- R$_6$ is alkyl;
- R$_7$ is hydrogen, alkyl, halogen, alkylthio, alkoxy, dialkylamino or formyl(alkyl)amino;
- R$_8$ is hydrogen or alkyl;

and wherein the number of aliphatic carbon atoms in R$_5$, R$_6$, R$_7$, and R$_8$, individually, does not exceed eight.

6. Symmetrical carbamates as defined in claim 1, wherein R and R' are phenyl or substituted phenyl, and R$_1$ and R$_2$ are alkyl groups containing from 1 to 10 carbon atoms, and wherein R$_1$ and R$_2$ are the same, and R and R' are the same.

7. Carbamates as defined in claim 1, wherein R$_2$ is selected from the groups consisting of unsubstituted and substituted alkyl, cycloalkyl, phenylalkyl; naphthylalkyl; unsubstituted and substituted phenyl and naphthyl; and wherein the substituents which can be present on said groups are selected from the class consisting of halogen, cyano, nitro, dialkylamino, alkyl, alkylthio and alkoxy.

8. Carbamates as defined in claim 1, wherein R$_2$ is alkyl.

9. Carbamates as defined in claim 1, wherein R, R' and R$_2$ are each alkyl.

10. Carbamates having pesticidal activity of the formula

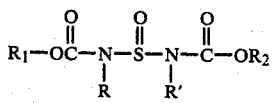

where R is an alkyl group having from 1 to 4 carbon atoms, and R' is selected from the class consisting of an alkyl group having from 1 to 8 carbon atoms, and phenyl, and R$_1$ and R$_2$ can be selected from the class consisting of a hydrocarbyl group containing from 1 to 12 carbon atoms, and a group containing the >C=N— radical, and where R and R' can be the same or different, and R$_1$ and R$_2$ can be the same or different.

11. Carbamates as defined in claim 10, wherein R$_1$ and R$_2$ are selected from the group consisting of alkyl, phenyl, alkylphenyl, naphthyl, alkylnaphthyl and alkoxyphenyl.

12. Carbamates as defined in claim 10, wherein R$_1$ is selected from the group consisting of alkylphenyl and alkoxyphenyl.

13. Carbamates as defined in claim 12, wherein R$_1$ is selected from the group consisting of 3-isopropylphenyl, 3-sec. butylphenyl and 2-isopropoxyphenyl.

14. Symmetrical carbamates as defined in claim 11, wherein R$_1$ and R$_2$ are the same, and R and R' are the same.

15. Carbamates as defined in claim 10, wherein R$_2$ is selected from the group consisting of alkyl, phenyl, alkylphenyl, naphthyl, alkylnaphthyl and alkoxyphenyl.

16. Carbamates as defined in claim 10, wherein R$_1$ is a group selected from the class having the formulae:

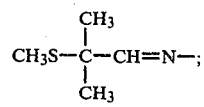

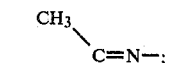

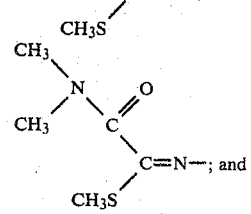

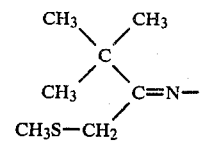

17. Carbamates as defined in claim 16, wherein R$_2$ is selected from the group consisting of alkyl, phenyl, alkylphenyl, naphthyl, alkylnaphthyl and alkoxyphenyl.

18. Carbamates as defined in claim 16, wherein R$_2$ is alkyl of from 1 to 12 carbon atoms and R is methyl.

19. Carbamates as defined in claim 16, wherein R$_1$ is the group having the formula:

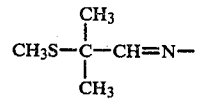

and R is methyl.

20. Symmetrical carbamates as defined in claim 16, wherein R$_2$ is the same as R$_1$, and R and R' are the same alkyl group.

21. Carbamates as defined in claim 20, wherein R and R' are each methyl.

22. N,N'-sulfinyldi-[S-methyl N''-(methylcarbamoyloxy)thioacetimidate].

23. N,N'-sulfinyldi-[2-methyl-2-(methylthio)propionaldehyde O-methylcarbamoyloxime].

24. N,N'-sulfinyldi-[S-methyl N'',N'''-dimethyl-N'''-methylcarbamoyloxy-1-thio-oximidate].

25. N,N'-sulfinyldi-[3,3-dimethyl-1-(methylthio)butanone O-methylcarbamoyloxime].

26. An insecticidal composition comprising an insecticidally effective amount of a carbamate as defined in claim 1, in admixture with a carrier.

27. An insecticidal composition comprising an insecticidally effective amount of a carbamate as defined in claim 10, in admixture with a carrier.

28. An insecticidal composition comprising an insecticidally effective amount of a carbamate as defined in claim 16, in admixture with a carrier.

29. The method of controlling insects which comprises applying to the sites of infestation an insecticidally effective amount of a compound as defined in claim 1.

30. The method of controlling insects which comprises applying to the sites of infestation an insecticidally effective amount of a compound as defined in claim 10.

31. The method of controlling insects which comprises applying to the sites of infestation an insecticidally effective amount of a compound as defined in claim 18.

* * * * *